(12) United States Patent
Ameer et al.

(10) Patent No.: US 8,772,437 B2
(45) Date of Patent: Jul. 8, 2014

(54) BIODEGRADABLE NITRIC OXIDE GENERATING POLYMERS AND RELATED BIOMEDICAL DEVICES

(71) Applicant: Northwestern University, Evanston, IL (US)

(72) Inventors: Guillermo Ameer, Chicago, IL (US); Melina Kibbe, Chicago, IL (US); Haichao Zhao, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/062,464

(22) Filed: Oct. 24, 2013

(65) Prior Publication Data

US 2014/0058049 A1    Feb. 27, 2014

Related U.S. Application Data

(62) Division of application No. 12/586,365, filed on Sep. 21, 2009, now Pat. No. 8,580,912.

(60) Provisional application No. 61/192,654, filed on Sep. 19, 2008.

(51) Int. Cl.

| | | |
|---|---|---|
| *C08G 69/44* | (2006.01) | |
| *A61L 29/08* | (2006.01) | |
| *A61L 31/16* | (2006.01) | |
| *C09D 179/02* | (2006.01) | |
| *A61L 31/06* | (2006.01) | |
| *A61L 29/16* | (2006.01) | |
| *C08G 63/685* | (2006.01) | |
| *A61L 31/10* | (2006.01) | |
| *C08G 73/02* | (2006.01) | |
| *A61L 31/14* | (2006.01) | |
| *A61L 27/34* | (2006.01) | |
| *A61L 27/54* | (2006.01) | |

(52) U.S. Cl.
CPC ............ *A61L 31/06* (2013.01); *A61L 29/085* (2013.01); *A61L 31/16* (2013.01); *C09D 179/02* (2013.01); *A61L 29/16* (2013.01); *A61L 2300/42* (2013.01); *C08G 63/6856* (2013.01); *A61L 2300/114* (2013.01); *A61L 31/10* (2013.01); *C08G 73/0206* (2013.01); *C08G 73/02* (2013.01); *A61L 31/148* (2013.01); *A61L 2300/416* (2013.01); *A61L 27/34* (2013.01); *A61L 27/54* (2013.01)

USPC ........... 528/291; 525/418; 525/419; 525/425; 525/437; 528/272; 528/288; 528/296

(58) Field of Classification Search
USPC .......... 525/418, 419, 425, 437; 528/272, 288, 528/291, 296

See application file for complete search history.

(56) References Cited

U.S. PATENT DOCUMENTS

| | | | |
|---|---|---|---|
| 4,632,964 A * | 12/1986 | Altschuler et al. ............ | 525/456 |
| 6,147,068 A | 11/2000 | Smith et al. | |
| 6,403,759 B2 | 6/2002 | Stamler et al. | |
| 6,534,178 B2 * | 3/2003 | Zhou et al. .................... | 428/413 |
| 7,186,789 B2 | 3/2007 | Hossainy et al. | |
| 2006/0276617 A1 * | 12/2006 | Yano et al. .................... | 528/272 |
| 2007/0053952 A1 | 3/2007 | Chen et al. | |
| 2007/0208420 A1 | 9/2007 | Ameer et al. | |
| 2009/0220426 A1 | 9/2009 | Fujishima et al. | |

FOREIGN PATENT DOCUMENTS

| | | |
|---|---|---|
| JP | 1993310898 | 11/1993 |
| JP | 2007501893 | 2/2007 |
| WO | 2007024501 | 3/2007 |
| WO | 2007082305 | 7/2007 |
| WO | 2007086306 | 8/2007 |
| WO | 2007092583 | 8/2007 |

OTHER PUBLICATIONS

McKee et al; Progress in Polymer Science, 2005, p. 507-539.*
English abstract of JP1993310898, 1 page.
US 20090220426 is the English language equivalent of WO2007086306.
Supplementary European Search Report for EP Application No: 09814911.5, mailed Dec. 13, 2012.
Zhao et al. "Biodegradable Nitric Oxide-Releasing Poly(Diol Citrate) Elastomers," Journal of Biomedical Materials Research, Jun. 2009, vol. 93, No. 3, pp. 356-363.
Reynolds, M.M., et al.; Biomacromolecules, 2006, vol. 7, p. 987-994.
International Search Report and Written Opinion for PCT/US2009/005240, dated Apr. 20, 2010.

* cited by examiner

*Primary Examiner* — Robert Jones, Jr.
(74) *Attorney, Agent, or Firm* — Casimir Jones, S.C.

(57) ABSTRACT

Disclosed herein is a biodegradable nitric oxide-generating polymer comprising a nitric oxide-releasing $N_2O_2^{31}$ (NONOate) functional group. The polymer can be applied to various medical devices for the treatment of various diseases such as thrombosis and restenosis.

18 Claims, 8 Drawing Sheets

Figure 3

| Samples | Density (g/cm$^3$) | Tensile strength (MPa) | Young's modulus (MPa) | Elongation (%) |
|---|---|---|---|---|
| POC | 1.219 | 2.93±0.09 | 1.85±0.09 | 367±15 |
| PPOC10 | 1.199 | 5.26±0.71 | 11.09±1.16 | 335±12 |
| PPOC20 | 1.204 | 12.01±0.47 | 51.78±4.93 | 298±15 |
| PPOC30 | 1.205 | 14.60±1.00 | 123.32±14.51 | 226±12 |
| PDC5 | 1.211 | 1.49±0.13 | 5.91±0.70 | 201±14 |
| PDC10 | 1.230 | 3.45±0.27 | 7.98±0.42 | 290±39 |
| PDC15 | 1.231 | 10.71±0.41 | 32.64±7.10 | 289±15 |

(a)

(b)

(c)

(d)

BIODEGRADABLE NITRIC OXIDE GENERATING POLYMERS AND RELATED BIOMEDICAL DEVICES

CROSS REFERENCE TO RELATED APPLICATIONS

The present application is a divisional of pending U.S. patent application Ser. No.: 12/586,365 filed Sep. 21, 2009, which claims benefit of expired U.S. Provisional Application Ser. No. 61/192,654 filed Sep. 19, 2008, each of which is incorporated herein by reference in its entirety.

FIELD OF THE INVENTION

This invention relates to certain spontaneous, biodegradable nitric oxide-generating citric acid-based polymers having a nitric oxide-releasing $N_2O_2^-$ functional group. Specifically, the invention relates to diazeniumdiolated aliphatic biodegradable elastomers for use in the prevention of thrombosis and restenosis.

BACKGROUND OF THE INVENTION

Many modern medical procedures require that synthetic medical devices remain in an individual undergoing treatment. Although a large number of polymeric materials are currently employed to prepare various blood-contacting implantable and extracorporeal medical devices, the thrombogenic nature of such materials can cause serious complications in patients, and ultimately functional failure. As a result, systemic anticoagulation regimens are almost always required clinically to reduce the risk of thrombus formation, especially in the case of vascular grafts. Furthermore, atherosclerosis is prevalent in all developed nations and is the leading cause of death and disability in the United States. Deaths due to cardiovascular disease account for 2,400 deaths per day, or 871,517 deaths per year, more than the next five leading causes of death combined. Currently, severe atherosclerotic coronary or peripheral arterial disease is treated with balloon angioplasty and stenting, bypass grafting, or endarterectomy.

However, the durability of these procedures is limited due to the development of neointimal hyperplasia which results from a cascade of events that ultimately leads to aggressive growth of the smooth muscle cells that line the artery wall and encroach on the lumen, causing restenosis or occlusion of the vessel. As evidence of the widespread nature of this problem, seventy-nine million Americans currently have cardiovascular disease and it is estimated that this number will increase significantly due to the growth of the aging population. Furthermore, it is estimated that $432 billion per year is spent in the United States on cardiovascular disease, with a significant portion being attributed to the cost of repeat interventions (Rosamond W. et al., *Circulation*, 2007, 115: e69-e171).

One promising therapeutic strategy to prevent thrombosis and neointimal hyperplasia has centered on the use of nitric oxide (NO), a molecule normally produced in endothelial cells that serves to protect the vessel wall. NO is a small, diffusible molecule with a very short half-life that is produced from L-arginine by one of three different NO synthase (NOS) enzymes. NO plays an important role as a potent vasodilator, inhibitor of vascular cell proliferation and migration, inhibitor of platelet aggregation, inhibitor of leukocyte chemotaxis, and stimulator of endothelial cell growth (Ahanchi S. et al., *Journal of Vascular Surgery*, 2007, 45: A64-73). As a result, compounds that spontaneously decompose to release NO are widely investigated for use in the vasculature.

Metal complexes, nitrosothiols, nitrosamines, and diazeniumdiolates are all samples of molecular structures that have been developed as effective NO donors (Wang P. et al., *Chem Rev,* 2002, 102: 1091-1134). Notably, diazeniumdiolate NO donors are particularly attractive for medical applications because they dissociate spontaneously under physiological conditions (i.e., 37° C., pH 7.4) to yield two moles of NO per mole of NO donor (Hrabie J. et al., *Chem Rev,* 2002, 102: 1135-1154). Using synthetic polymeric materials that can release or generate NO locally for extended periods may provide the ultimate method to greatly reducing the risk of thrombosis on the surface of many types of biomedical implants that are in contact with blood, as well as prevent the development of neointimal hyperplasia.

To date, diazeniumdiolated polymers such as polyurethane (Jun H. et al., *Biomacromolecules,* 2005, 6: 838-844), poly (ethylenimine) (Davies K. et al., *J Med Chem,* 1996, 39:1148-1156), polymethacrylate (Parzuchowski P. et al., J Am Chem Soc, 2002, 124: 12182-12191), poly(vinyl chloride) (Saavedra J. et al., *J Org Chem,* 1999, 64: 5124-5131), diamino cross-linked polydimethoxysilane (Smith D. et al., *Biomaterials,* 2002, 23: 1485-1494), dendrimers (Stasko N. et al., *J Am Chem Soc,* 2006, 128: 8265-8271) have been the most studied class of NO donor agents. However, no diazeniumdiolated aliphatic biodegradable elastomers for generating NO have been prepared.

SUMMARY OF THE INVENTION

In light of the foregoing, it is an object of the present invention to provide a biodegradable nitric oxide-generating polymer comprising a nitric oxide-releasing $N_2O_2^-$ (NONOate) functional group for the prevention of thrombosis and restenosis. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Accordingly, it is an object of the invention to provide a method of preparing an amino-containing citric acid-based elastomer comprising the polycondensation of citric acid, an aliphatic diol, and an amino-containing monomer.

It is another object of the invention to provide a method of controlling mechanical properties and NO-release of a biodegradable amino-containing citric acid-based elastomer comprising the presence of a certain amount of a secondary amine-containing unit.

It is yet another object of the invention to provide a method of preparing a coated ePTFE graft comprising coating of a NO-releasing elastomer as described herein to the graft, crosslinking and treating with NO.

It is still another object of the invention to provide a biomedical device comprising a NO-releasing elastomer.

BRIEF DESCRIPTION OF THE DRAWINGS

FIG. 3 summarizes the mechanical properties of PDC with various amino diol compositions and PPOC with various proline contents.

DETAILED DESCRIPTION OF CERTAIN EMBODIMENTS

As illustrated by several non-limiting embodiments, this invention relates to a biodegradable nitric oxide-generating polymer comprising a nitric oxide-releasing $N_2O_2^-$ functional group. Nitric oxide (NO) is a well-known inhibitor of platelet adhesion and contributes significantly to the thromboresistant nature of a healthy endothelium. Nitric oxide is also a potent inhibitor of neointimal hyperplasia, a process that commonly results in restenosis of arteries following vascular interventions such as balloon angioplasty and stenting, bypass grafting, and endarterectomies. The polymers of the invention, which release or generate NO locally at their surface, therefore exhibit greatly enhanced thromboresistivity and can reduce neointimal hyperplasia caused by device damage to blood vessel walls. Such NO-releasing biodegradable polymers of the instant invention can provide stability and structural integrity within a mechanically dynamic environment without irritation to the hosting tissues and exhibit mechanical properties similar to those of soft tissues.

More particularly, the instant invention relates to biodegradable elastomeric polymer having the formula I

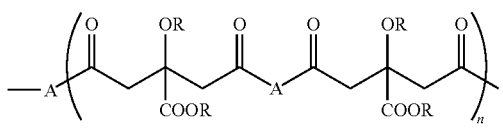

wherein R is hydrogen or a polymer, each A is independently selected from a NONOate-containing amine diol unit and an aliphatic diol unit, and n is an integer greater than 1, provided that at least one each of NONOate-containing amine diol unit and an aliphatic diol unit is present. In specific embodiments, each A is independently selected from —O—$(CH_2)_8$—O— and —$(CH_2)_2$—N[(N$^+$=N—O$^-$)O$^-$]—$(CH_2)_2$—N$^+$H$_2$—$(CH_2)_2$—O—. The invention also relates to specific amine crosslinkable elastomers of a citric acid-aliphatic diol pre-polymer. In a specific embodiment, the amine crosslinker of the citric acid-aliphatic diol pre-polymer is proline, and preferably trans-4-hydroxy-L-proline.

As it relates to certain embodiments, a polymer of the invention can be a citric acid-based biodegradable elastomeric polyester, with tunable mechanical properties and in vitro and in vivo biocompatibility. Such polymers can be prepared with a variety of amine units, both single hydroxyl and diols alike, with various aliphatic diols, as for example, those disclosed in U.S. Ser. No. 10/945,354, filed on Sep. 20, 2004, the entirety of which is incorporated herein by reference. Regardless, NO-generation can be achieved by incorporation of an NH functional group into the polymer network. An NO-releasing elastomer can be formed, cast, or otherwise shaped to form a monolithic device, such as an implantable device (e.g. a drug depot) or indwelling devices, (e.g. catheters, or extracorporeal tubing sets kidney dialysis). An elastomeric polymer can also be applied as a coating on another substrate, such as polymer substrate (e.g. expanded polytetrafluoroethylene) or the surface of metal implant. The elastomer of the instant invention can also act as biofilm for wrapping the blood vessel.

Figure 1:
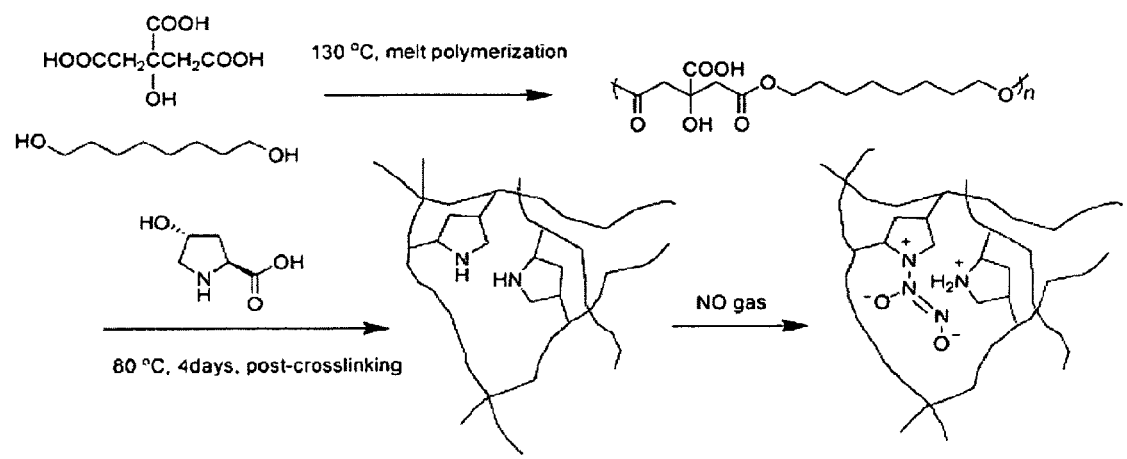
FIGS. 1 and 2 are schematics illustrating the methods used to prepare the NONOate PPOC and NONOate PDC.
Figure 2:
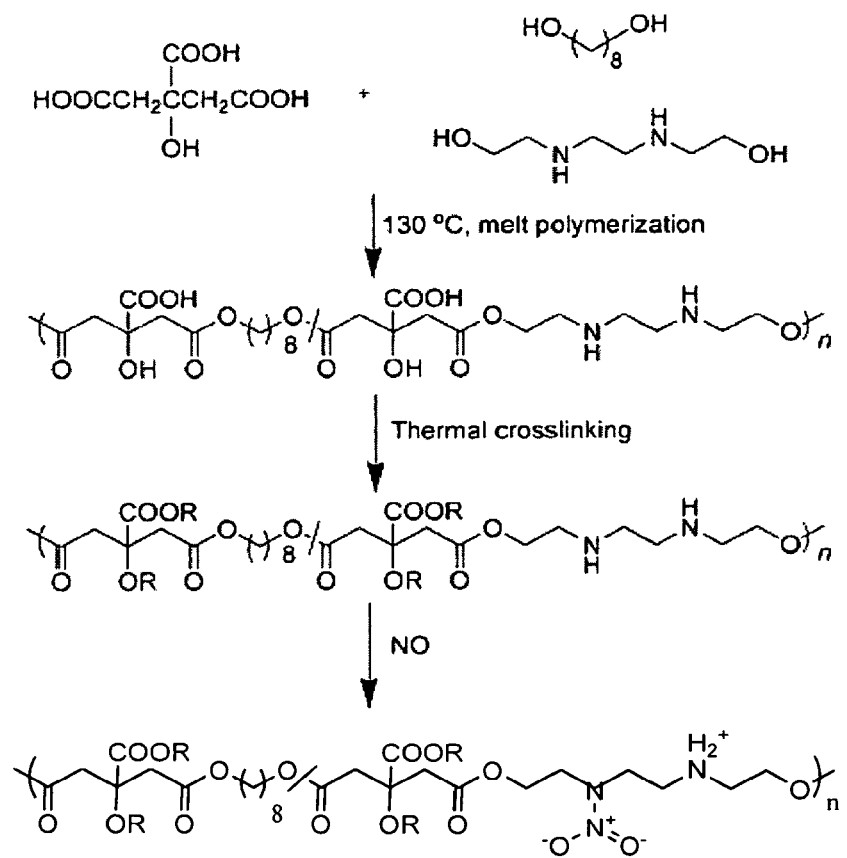

With respect to certain non-limiting embodiments, this invention can relate to the preparation of a spontaneous, biodegradable, NO-releasing citric acid-based elastomers. The elastomer can be obtained by synthesizing prepolymer of citric acid and aliphatic diol, followed by addition of crosslinkable amine units during the post-crosslinking and the reaction of NO gas (FIG. 1). The elastomers can also be prepared by polycondensation of citric acid, aliphatic diol and amino diol, followed by crosslinking and NO treating (FIG. 2).

Figure 4:
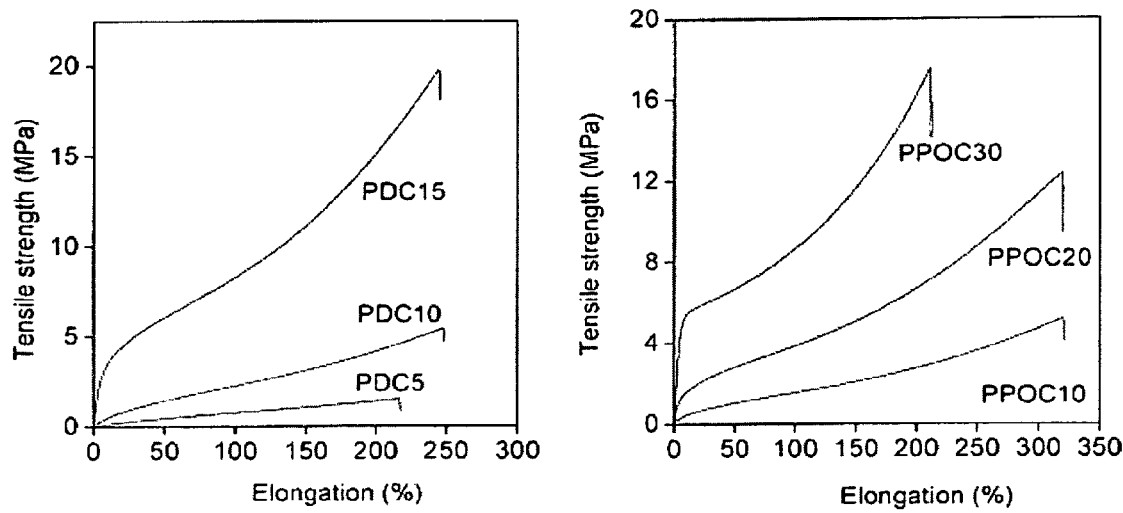
FIG. 4 shows the tensile-strain curves of PDC and PPOC.

FIG. 3 summarizes the density and mechanical properties of the elastomers, while FIG. 4 depicts the typical tensile-strain curves of the elastomers with different compositions. As shown in FIG. 3, the mechanical properties of elastomers can be well controlled by adjusting the proline or amine diol contents. Notably, all the secondary amine containing elastomers are stronger than citric acid/1,8-octanediol-based elastomer (POC), although the elongation decreases slightly. The tensile strength of PDC is as high as 10.71 MPa and Young's modulus range from 5.91 to 32.64 MPa under the synthesis conditions, while the tensile strength and Young's modulus increases from about 4 times to more than 60 times against those of POC.

Figure 5:
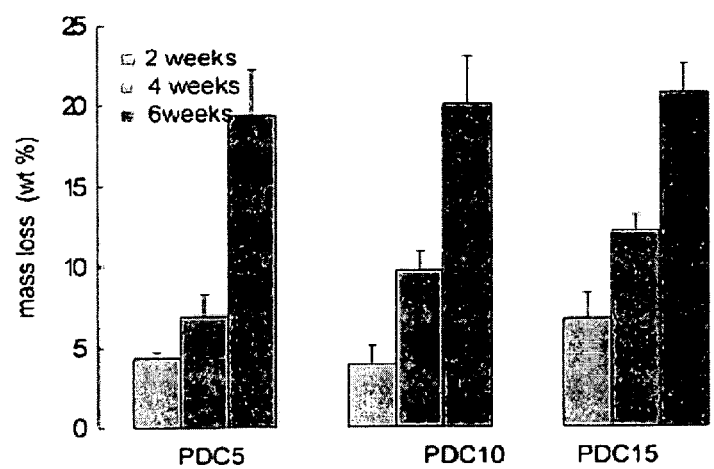
FIG. 5 demonstrates the degradation properties of PDC.

The degradation characterization of the elastomeric PDC is presented in FIG. 5. The elastomer with various amino diol contents shows similar degradation rates. The mass loss of the elastomers is between 4-6% after the first two weeks in PBS at 37° C., 7-12% after 4 weeks, and 18-22% after 6 weeks.

HAEC cell adhesion and proliferation on the elastomers is observed after 1 day and 1 week. Photomicrographs in FIG. 6 (a) and (b) show that both types of cells attach and display a normal phenotype on the elastomeric PPOC20 and PDC10. After 1 week, the cells are confluent (FIG. 6 (c) and (d)).

Figure 7:
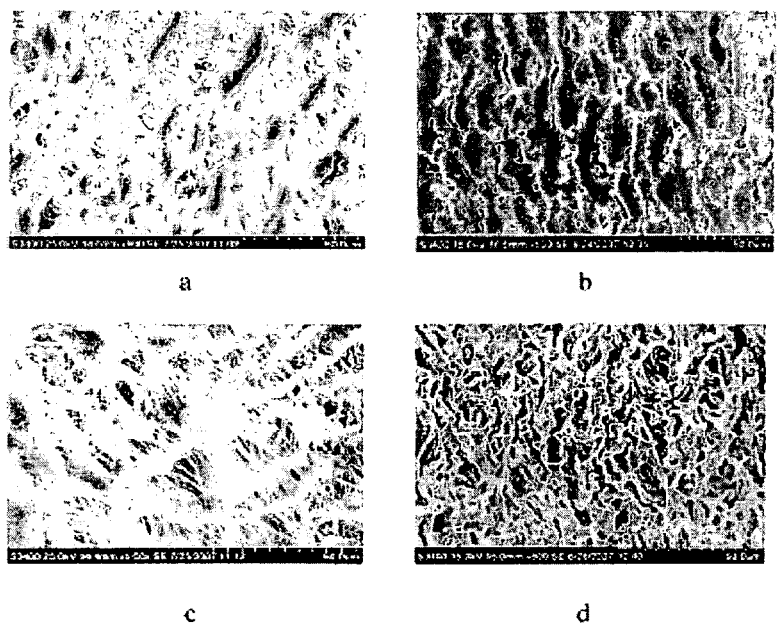
FIG. 7 is SEM images of (a) inner surface of ePTFE grafts control; (b) inner surface of coated ePTFE grafts; (c) cross-section of ePTFE grafts control; and (d) cross-section of coated ePTFE grafts.

FIG. 7 shows the microarchitecture of ePTFE before and after coated with PDC10, illustrating that the microarchitecture of the fibril and node network of coated ePTFE is preserved within the deposited POC layer.

Figure 8:
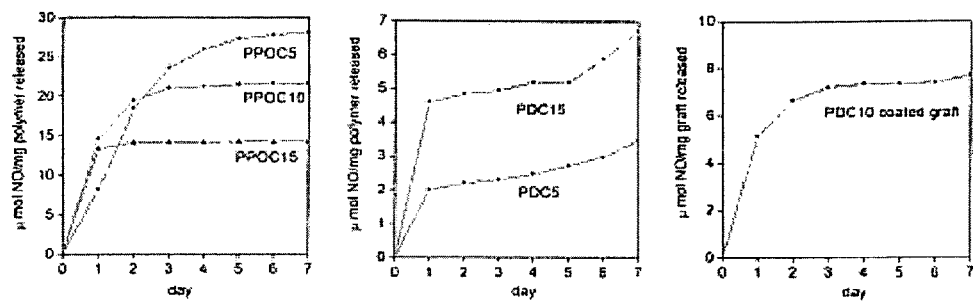
FIG. 8 is the NO release from films and PDC10 coated ePTFE.

FIG. 8 shows the NO release properties of NONOate elastomers and coated ePTFE. PPOC10 continues to release NO for 7 days. Almost 90% NO is released in the first 2 days for the PPOC 20 and PPOC 30. PDC5 and PDC 15 show similar release tendency.

An ePTFE graft is porous and is permeable to gases or organic solvent. Furthermore, the pore size of ePTFE can be adjusted by varying the amount of stretching during manufacture. It is possible that liquid prepolymer solution may also permeate through ePTFE and obtain a polymer modified ePTFE after post crosslinking. As seen in FIG. 8, NO release from NONOate PDC10 coated ePTFE in the coated graft is about 20 wt. %. Most of the NO is released from the graft in the first 3 days.

EXAMPLES OF THE INVENTION

Materials: 1,8-octanediol (98%), N,N'-bis(2-hydroxyethyl)-ethylenediamine, trans-4- hydroxy-L-proline and citric acid (99.5%) are purchased from Sigma-Aldrich (St. Louis, Mo., USA) and used as received. ePTFE graft is purchased from W. L. Gore & Associates, Inc. (3300 E. Sparrow Ave, Flagstaff, Ariz., 86004, USA).

The following non-limiting examples and data illustrate various aspects and features relating to the compositions and/or methods of the present invention, including the preparation and use of a citric acid-based biodegradable elastomeric polyester, as describe herein. Related examples, procedures and methods are described in co-pending applications U.S. Ser. Nos. 10/945,354, filed Sep. 20, 2004 and 11/704,039, filed on Feb. 8, 2007, both of which are incorporated herein by reference.

Example 1

Preparation of proline-containing poly(1,8-octanediol citrate) (PPOC). The monomers with the molar ratio of citric acid:1,8-octanediol : trans-4-hydroxy-L-proline equal to 100: 100:10 (PPOC10), 100:100:20 (PPOC2O), 100:100:30 (PPOC3O), respectively, are used for preparation of the hydroxyproline-crosslinked elastomeric films. As an example, 0.1 mol of 1,8-octanediol and 0.1 mol of citric acid are added to a 100 ml round bottom flask and exposed to a constant flow of nitrogen gas. The mixture is melted under vigorous stirring at 160-165° C. Following melting, the mixture is polymerized at 130° C. for 30 minutes to get prepolymer, and then 0.02 mol of trans-4-hydroxy-L-proline is added. The system is allowed to polymerize for another 30 minutes to get proline-containing prepolymer. The prepolymer with various proline contents is further crosslinked at 80° C. for 4 days to afford the crosslinked elastomer.

Example 2

Preparation of amino diol-functionalized poly(diol citrate) (PDC). The monomers with the molar ratio of citric acid:1, 8-octanediol: N,N-bis(2-hydroxyethyl)-ethylenediamine equal to 100:95:5 (PDC5), 100:90:10 (PDC10), 100:85:15 (PDC15), respectively, are used for preparation of the crosslinked elastomeric films. As and example, 0.09 mol of 1,8-octanediol and 0.1 mol of citric acid are added to a 100 ml round bottom flask and exposed to a constant flow of nitrogen gas. The mixture is melted under vigorous stirring at 160-165° C. Following melting, 0.01 mol N,N'-bis(2-hydroxyethyl)-ethylenediamine is added to the mixture and the complex is polymerized at 130° C. for 40 minutes in $N_2$ atmosphere to get prepolymer of PDC10. The prepolymer is then casted into a glass plate and post-polymerized at 80° C. for 4 days to create crosslinked elastomeric PDC10.

Example 3

Characterization of elastomers. Elastomer density is measured by a Mettler Toledo balance with a density determination kit (Greifensee, Switzerland) based on Archimedes' principle. Absolute ethanol is used as auxiliary liquid. Tensile mechanical tests are conducted according to ASTM D412a on an Instron 5544 mechanical tester equipped with SOON load cell (Instron Canton, Mass.). The sample (26-4-1.0 mm, length-width-thickness) is pulled at a rate of 500 mm/mm. Values are converted to stress-strain and a Young's modulus is calculated from the initial slope. 4-6 samples are measured and averaged.

Example 4

In vitro degradation. Disk-shaped specimens (6 mm in diameter, about 1 mm thickness) are placed in a tube containing 10 ml phosphate buffer saline (pH 7.4) and are incubated at 37° C. After incubation, samples are washed with water and freeze-dried for 1 week. Mass loss is calculated by comparing the initial mass ($W_o$) with the mass measured at a given time point (Wt), as shown in Equation (1). Five individual experiments are performed for the degradation test. The results are presented as means.

$$\text{Mass loss (\%)} = [(W_o - Wt)/W_o] \times 100 \quad \text{Equation (1)}$$

Example 5

Figure 6:
FIG. 6 Photomicrographs of HAEC cultured on (a) PPOC 20 and (b) PDC 10 for 24 h (×200), and (c) PPOC 20 and (d) PDC10 for 1 week.
Figure 6:
Figure 6:
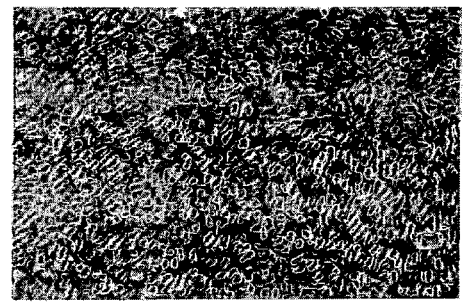
Figure 6:
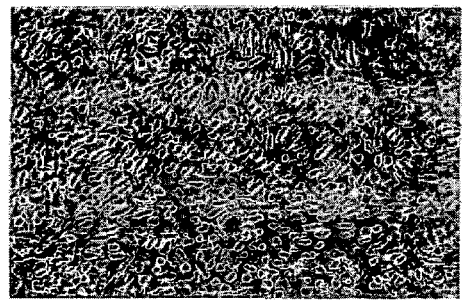

In vitro cell culture. Human aortic endothelial cells (HAEC) (Clonetics, Waikersville, Md.) are cultured with EBM-2 culture medium. (Clonetics, Walkersville, Md.). Cell culture is maintained in a water-jacket incubator equilibrated with 5% CO2 at 37° C. PDC films are cut into small pieces (1-2 $cm^2$) and placed in cell culture dishes (6 cm in diameter). All polymer samples are sterilized by incubation in 70% ethanol for 30 mm followed by UV light exposure for another 30 minutes. HAEC at a density of $1.0 \times 10^6$ cells/ml of HAEC, respectively, are added to the elastomeric films in tissue culture dishes. Approximately 30 minutes after cell seeding, 5 ml of culture medium are added to the culture dishes. The morphology of attached cells is observed and recorded at 1 day and 7 days after cell seeding with an inverted light microscope (Nikon Eclipse, TE2000-U) equipped with a Photometrics CoolSNAP HQ (Silver Spring, Md.) (FIG. 6).

Example 6

Preparation of PDC-coated ePTFE. The lumen of standard-wall non-stretch ePTFE grafts (Gore-Tex, W. L. Gore &Associates, Flagstaff, Ariz., 6 mm inner diameter) is coated by 10% PDC10 ethanol solution. One end of ePTFE in 6 cm length is sealed, 15 ml 10% PDC10 ethanol solution is injected into ePTFE through the other end, and the polymer solution is permeated through the inter layer of the grafts. After removing the PDC solution, the grafts are left out at room temperature for 24 hours to evaporate the ethanol. Subsequent post-polymerizeation at 80° C. for 3 days affords a PDC coated ePTFE.

Example 7

Preparation of NONOate PDC or coated ePTFE and its NO release. The PDC films and PDC coated ePTFE grafts were treated with NO gas in acetonitrile at room temperature for 48 h. The treated films were then dried in vacuum at room temperature for 48 h. The films and coated ePTFE were incubated in PBS at 37° C. for 1-7 days. Release of NO from the films was measured using the Griess assay, which quantifies the nitrites, the primary degradation product of NO.

Results

The invention provides citric acid based NO releasing biodegradable elastomers, e.g., the proline crosslinked poly(1,8-octanediol citrate) (PPOC) and amine diol containing poly (diol citrate) (PDC). The mechanical properties of the elastomers can depend on the secondary amine contents and the elastomers show good biocompatibility based in vitro cell culture. NO is successfully generated from the polymer films and coated ePTFE. The elastomer has mechanical properties similar to those of commercially available synthetic vascular grafts and may be useful for a wide variety of cardiovascular applications, including but not limited to use in coating, vascular grafts, and tubing.

What is claimed is:

1. A biocompatible elastomeric polymer comprising polyesters of citric acid and aliphatic diol, wherein said polyesters are crosslinked by a secondary-amine-containing crosslinker.

2. The method of claim 1 wherein the aliphatic diol is 1,8-octanediol.

3. The polymer of claim 1 wherein the crosslinker is trans-4-hydroxy-L-proline.

4. The polymer of claim 3 wherein the aliphatic diol is 1,8-octanediol.

5. A method of preparing a crosslinked elastomer of a citric acid aliphatic diol pre-polymer comprising:
   a) synthesizing a prepolymer of citric acid and aliphatic diol;
   b) post-polymerizing the prepolymer with a crosslinker comprising a secondary amine group to form a post polymer, wherein the secondary amine group does not participate in the post-polymerization reaction.

6. The method of claim 5 wherein the crosslinker is trans-4-hydroxy-L-proline.

7. The method of claim 6 wherein the aliphatic diol is 1,8-octanediol.

8. A method of preparing a biocompatible elastomeric polymer of the formula:

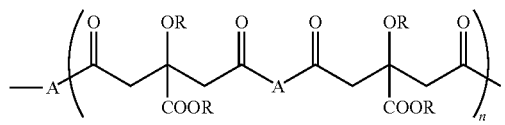

wherein R is hydrogen or a polymer, each A is independently selected from a NONOate-containing amine diol unit and an aliphatic diol unit, and n is an integer greater than 1, provided that at least one each of NONOate-containing amine diol unit and an aliphatic diol unit is present, comprising:
   a) polycondensing a citric acid, an aliphatic diol and an amino diol;
   b) crosslinking; and
   c) treating the crosslinked polymer with NO gas.

9. The method of claim 8 wherein the aliphatic diol is 1,8-octanediol.

10. The method of claim 9 wherein the amine diol is N,N-bis(2-hydroxyethyl-ethylenediamine.

11. A biomedical device wherein at least one surface of the device has deposited thereon a coating comprising a NO-releasing elastomer selected from:
   a) a compound having formula:

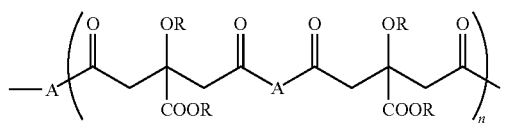

Wherein R is hydrogen or a polymer, each A is independently selected from a NONOate-containing amine diol unit and an aliphatic diol unit, and n is an integer greater than 1, provided that at least one each of NONOate-containing amine diol unit and an aliphatic diol unit is present; and
   b) an elastomeric polymer comprising polyesters of citric acid and aliphatic diol crosslinked by a secondary-amine containing crosslinker.

12. The biomedical device of claim 11 wherein A selected from —O—(CH$_2$)$_8$—O— and —O—(CH$_2$)$_2$—N[(N$^+$=N—O$^-$)O-]—(CH$_2$)$_2$—N$^+$H$_2$—(CH$_2$)$_2$—O—.

13. The biomedical device of claim 11 wherein the crosslinker is trans-4-hydroxy-L-proline.

14. The biomedical device of claim 13 wherein the aliphatic diol is 1,8-octanediol.

15. The biomedical device of claim 12 wherein the device is an implantable device.

16. The biomedical device of claim 14 wherein the device is an implantable device.

17. The method of claim 5, further comprising:
   c) reacting the post-polymer with NO gas.

18. A device comprising the biocompatible elastomeric polymer of claim 1.

* * * * *

UNITED STATES PATENT AND TRADEMARK OFFICE
CERTIFICATE OF CORRECTION

PATENT NO.        : 8,772,437 B2
APPLICATION NO.   : 14/062464
DATED             : July 8, 2014
INVENTOR(S)       : Guillermo Ameer, Melina Kibbe and Haichao Zhao It is certified that error appears in the above-identified patent and that said Letters Patent is hereby corrected as shown below:

On the title page item (57) should read

ABSTRACT

Disclosed herein is a biodegradable nitric oxide-generating polymer comprising a nitric oxide-releasing $N_2O_2^-$ (NON-Oate) functional group. The polymer can be applied to various medical devices for the treatment of various diseases such as thrombosis and restenosis.

In the Claims:
Column 7, lines 25 to 32, should read:

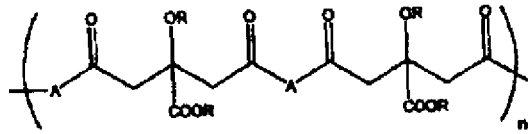

Column 8, lines 9 to 16, should read:

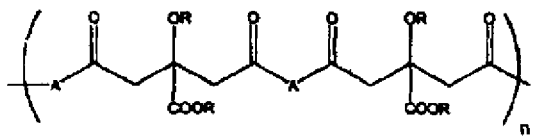

Signed and Sealed this
Sixteenth Day of September, 2014

Michelle K. Lee
*Deputy Director of the United States Patent and Trademark Office*